(12) United States Patent
Minagawa (10) Patent No.: US 9,321,872 B2
(45) Date of Patent: *Apr. 26, 2016

(54) SURFACE MODIFICATION METHOD AND SURFACE-MODIFIED ELASTIC BODY

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 235 days.

This patent is subject to a terminal disclaimer.

(21) Appl. No.: 13/756,837

(22) Filed: Feb. 1, 2013

(65) Prior Publication Data
US 2013/0203883 A1 Aug. 8, 2013

(30) Foreign Application Priority Data
Feb. 2, 2012 (JP) ................. 2012-021228

(51) Int. Cl.
| | | |
|---|---|---|
| C08J 3/28 | (2006.01) |
| C08F 2/50 | (2006.01) |
| C08F 255/10 | (2006.01) |
| C08F 291/18 | (2006.01) |
| C08F 279/02 | (2006.01) |
| B60C 1/00 | (2006.01) |
| C08J 7/18 | (2006.01) |
| B60C 11/03 | (2006.01) |
| B60C 11/13 | (2006.01) |
| A61L 29/04 | (2006.01) |
| A61L 29/14 | (2006.01) |

(52) U.S. Cl.
CPC .............. *C08F 279/02* (2013.01); *A61L 29/042* (2013.01); *A61L 29/14* (2013.01); *B60C 1/0016* (2013.04); *B60C 11/0306* (2013.04); *B60C 11/1307* (2013.04); *B60C 11/1346* (2013.04); *B60C 11/1353* (2013.04); *C08F 2/50* (2013.01); *C08F 255/10* (2013.01); *C08F 291/18* (2013.01); *C08J 7/18* (2013.01); *A61L 2400/18* (2013.01); *B60C 2011/0369* (2013.04); *C08J 2300/26* (2013.01); *C08J 2433/02* (2013.01); *C08J 2433/14* (2013.01)

(58) Field of Classification Search
CPC ........ C08F 2/50; C08F 255/10; C08F 279/02; C08F 291/18; C08J 7/16; C08J 2300/26; C08J 2433/02; C08J 2433/14; B60C 1/0016; B60C 11/0306; B60C 11/1307; B60C 11/3046; B60C 11/1353; B60C 2011/0369; A61L 29/042; A61L 29/14; A61L 2400/018
See application file for complete search history.

(56) References Cited

U.S. PATENT DOCUMENTS

| | | | |
|---|---|---|---|
| 3,418,066 A | 12/1968 | Caldwell et al. |
| 5,100,689 A * | 3/1992 | Goldberg et al. ............... 600/36 |
| 5,637,460 A | 6/1997 | Swan et al. |
| 5,885,566 A | 3/1999 | Goldberg |
| 5,967,714 A | 10/1999 | Ottersbach et al. |
| 6,001,894 A | 12/1999 | Ottersbach et al. |
| 6,203,856 B1 | 3/2001 | Ottersbach et al. |
| 6,358,557 B1 | 3/2002 | Wang et al. |
| 6,808,738 B2 * | 10/2004 | DiTizio et al. ............... 427/2.24 |
| 8,840,927 B2 * | 9/2014 | DiTizio et al. ............... 424/486 |
| 2002/0161065 A1 | 10/2002 | DiTizio et al. |
| 2004/0086568 A1* | 5/2004 | Ditizio et al. ............... 424/486 |
| 2004/0106732 A1 | 6/2004 | Tsuji et al. |
| 2007/0003592 A1 | 1/2007 | Hissink |
| 2007/0116971 A1 | 5/2007 | Yoshikawa et al. |
| 2008/0016644 A1 | 1/2008 | Mizote et al. |
| 2008/0312377 A1 | 12/2008 | Schmidt et al. |
| 2011/0160357 A1 | 6/2011 | Gerster et al. |
| 2013/0203883 A1 | 8/2013 | Minagawa |
| 2013/0274367 A1 | 10/2013 | Minagawa et al. |
| 2013/0310772 A1 | 11/2013 | Minagawa |
| 2014/0039084 A1 | 2/2014 | Minagawa |
| 2014/0128493 A1 | 5/2014 | Minagawa |
| 2015/0203612 A1 | 7/2015 | Minagawa |

FOREIGN PATENT DOCUMENTS

| | | |
|---|---|---|
| GB | 1120804 | 1/1965 |
| GB | 1120803 A | 7/1968 |
| JP | 61-209667 A | 9/1986 |
| JP | 62-87163 A | 4/1987 |
| JP | 63-92658 A | 4/1988 |

(Continued)

OTHER PUBLICATIONS

International Search Report dated Dec. 3, 2013, for International Application No. PCT/JP2013/074219.

(Continued)

*Primary Examiner* — Sanza McClendon (74) *Attorney, Agent, or Firm* — Birch, Stewart, Kolasch & Birch, LLP (57) ABSTRACT

The present invention aims to provide a surface modification method for a rubber vulcanizate or a thermoplastic elastomer, which can impart various functions such as sliding properties and biocompatibility according to its use. The present invention relates to a surface modification method for modifying a rubber vulcanizate or a thermoplastic elastomer as an object to be modified, the method including: Step 1 of forming polymerization initiation points on a surface of the object to be modified; Step 2 of radical polymerizing monomers starting from the polymerization initiation points to grow polymer chains on the surface of the object to be modified; and Step 3 of functionalizing the polymer chains.

27 Claims, 2 Drawing Sheets

(56) References Cited

FOREIGN PATENT DOCUMENTS

| | | |
|---|---|---|
| JP | 5-179055 A | 7/1993 |
| JP | 6-25450 A | 2/1994 |
| JP | 8-1793 A | 1/1996 |
| JP | 9-67457 A | 3/1997 |
| JP | 10-251350 A | 9/1998 |
| JP | 10-298320 A | 11/1998 |
| JP | 2001-95621 A | 4/2001 |
| JP | 2002-145971 A | 5/2002 |
| JP | 2003-2903 A | 1/2003 |
| JP | 2003-510378 A | 3/2003 |
| JP | 2004-528418 A | 9/2004 |
| JP | 2004-298220 A | 10/2004 |
| JP | 2005-213516 A | 8/2005 |
| JP | 2007-145884 A | 6/2007 |
| JP | 2009-30074 A | 2/2009 |
| JP | 2009-138169 A | 6/2009 |
| JP | 2010-23710 A | 2/2010 |
| JP | 2010-142537 A | 7/2010 |
| JP | 2010-142573 A | 7/2010 |
| JP | 2010-150349 A | 7/2010 |
| JP | 2011-189562 A | 9/2011 |
| JP | 2011-241190 A | 12/2011 |
| JP | 2012-162646 A | 8/2012 |
| WO | 2007/072613 A1 | 6/2007 |
| WO | WO 2011/038483 | 4/2011 |
| WO | WO 2012/091169 A1 | 7/2012 |

OTHER PUBLICATIONS

U.S. Office Action dated Jun. 24, 2015, for U.S. Appl. No. 14/118,136.

U.S. Office Action dated Sep. 21, 2015, for U.S. Appl. No. 14/107,746.

Allmér et al., "Surface Modification of Polymers. I. Vapour Phase Photografting with Acrylic Acid," Journal of Polymer Science: Part A: Polymer Chemistry, vol. 26, 1988, pp. 2099-2111.

International Search Report, mailed on Jul. 24, 2012, for International Application No. PCT/JP2012/064030.

U.S. Notice of Allowance, issued Dec. 26, 2014, for U.S. Appl. No. 13/956,974.

U.S. Office Action (Requirement for Restriction/Election), issued May 9, 2014, for U.S. Appl. No. 13/956,974.

U.S. Office Action, issued Apr. 17, 2015, for U.S. Appl. No. 13/775,451.

U.S. Office Action, issued Aug. 25, 2014, for U.S. Appl. No. 13/956,974.

\* cited by examiner

SURFACE MODIFICATION METHOD AND SURFACE-MODIFIED ELASTIC BODY

TECHNICAL FIELD

The present invention relates to a surface modification method; and surface-modified elastic bodies such as catheters and gaskets for syringes each of which has at least partially a surface modified by the surface modification method, and tires which have at least partially a groove surface modified by the surface modification method.

BACKGROUND ART

For parts that slide while maintaining seal, such as gaskets each of which is integrated with a syringe plunger and forms a seal between the plunger and the barrel, elastic bodies (e.g. rubber) are used in great consideration of sealing properties. Such elastic bodies, however, have a slight problem in their sliding properties (see Patent Literature 1). Hence, a sliding property improver (e.g. silicone oil) is applied to the sliding surface, but it is pointed out that silicone oil can have a bad influence on recently marketed bio-preparations. On the other hand, a gasket to which a sliding property improver is not applied is poor in the sliding properties. Thus, the plunger cannot be pushed smoothly so that it pulsates upon administration, thereby causing problems such as inaccuracy in the injection amount and infliction of pain on patients.

In order to simultaneously satisfy such conflicting requirements, that is, the sealing properties and the sliding properties, one technique is proposed in which a self-lubricating PTFE film is applied (see Patent Literature 2). Such a film, however, is generally expensive and causes an increase in the production cost of processed products, and thus its application range is limited. Also, products covered with the PTFE film might not be reliable in the case that the products are used in applications in which sliding or the like motion is repeated and durability is thereby required. Another problem is that PTFE is vulnerable to radiation and thus it cannot be sterilized by radiation.

Furthermore, the parts may be used in applications requiring sliding properties in the presence of water. Specifically, water can be delivered without a loss by reducing the fluid resistance of the inner surface of a pre-filled syringe or the inner surface of a pipe or tube for delivering water (e.g. catheters), or by making its contact angle with water high or greatly low. Also, drainage of water on wet roads and of snow on snowy roads can be improved by reducing the fluid resistance of the groove surface of tires, or by making its contact angle with water high or greatly low. This results in enhanced grip and enhanced hydroplaning properties, leading to better safety. In addition, less sticking of wastes and dusts is expected as a result of reducing the sliding resistance of the sidewall surface of a tire or a wall of a building, or as a result of making its contact angle with water high.

Further advantageous effects can be expected, such as less pressure loss when water, an aqueous solution, or the like is delivered through a diaphragm such as a diaphragm pump or a diaphragm valve; easy sliding of skis or a snowboard by enhancing the sliding properties of the sliding surface thereof; better noticeability of a road sign or a signboard by enhancing the sliding properties thereof to allow snow to slide easily; reduction in water resistance or drag and less sticking of bacteria on the outer peripheries of a ship by reducing the sliding resistance of the outer peripheries or by making their contact angle with water high; and swimsuits with reduced water resistance or drag by improving the sliding properties of the thread surface thereof.

CITATION LIST

Patent Literature

Patent Literature 1: JP 2004-298220 A
Patent Literature 2: JP 2010-142537 A

SUMMARY OF INVENTION

Technical Problem

The present invention aims to solve the above problems and provide a surface modification method for a rubber vulcanizate or a thermoplastic elastomer, which can impart various functions (e.g. sliding properties, biocompatibility) according to its use. The present invention also aims to provide surface-modified elastic bodies such as catheters and gaskets for syringes each of which has at least partially a surface modified by the surface modification method, and tires which have at least partially a groove surface modified by the surface modification method.

Solution to Problem

The present invention relates to a surface modification method for modifying a rubber vulcanizate or a thermoplastic elastomer as an object to be modified, the method including: Step 1 of forming polymerization initiation points on a surface of the object to be modified; Step 2 of radical polymerizing monomers starting from the polymerization initiation points to grow polymer chains on the surface of the object to be modified; and Step 3 of functionalizing the polymer chains.

Preferably, the Step 1 includes irradiating the surface of the object to be modified with LED light at 300 to 400 nm to form the polymerization initiation points from a photosensitizer on the surface, and the Step 2 includes irradiating the monomers with LED light at 300 to 400 nm to radical polymerize the monomers starting from the polymerization initiation points to grow the polymer chains.

The rubber vulcanizate or the thermoplastic elastomer preferably contains an allylic carbon atom which is a carbon atom adjacent to a double bond.

The photosensitizer is preferably a benzophenone compound represented by the following formula (1):

wherein $R^1$ to $R^5$ and $R^{1\prime}$ to $R^{5\prime}$ are the same as or different from each other and each represent a hydrogen atom, an alkyl group, a halogen, a hydroxy group, a primary, secondary, or tertiary amino group, a mercapto group, or a hydrocarbon group that may contain an oxygen atom, a nitrogen atom, or a sulfur atom; and any two adjacent groups thereof may be joined to each other to form a cyclic structure together with the carbon atoms to which they are bonded.

The Step 2 preferably includes adding a reducing agent or an antioxidant for radical polymerization of the monomers.

The reducing agent or the antioxidant is preferably at least one selected from the group consisting of riboflavin, ascorbic acid, α-tocopherol, β-carotene, and uric acid.

In the surface modification method, preferably, during or before the light irradiation, an inert gas is inserted into a reaction container and a reaction solution to replace the atmosphere therein with the inert gas, followed by polymerization.

The Step 3 preferably includes salifying side chains of the polymer chains.

The Step 3 may be performed by introducing a functionalized group as a result of: for example, salifying side chains of the polymer chains using an alkali metal salt or an antibacterial metal salt; bringing side chains of the polymer chains into contact with aqueous ammonia and then salifying the side chains; salifying side chains of the polymer chains using an alkaline salt; salifying side chains of the polymer chains using a nitrate, a carbonate, or a halogenated salt; or salifying side chains of the polymer chains using silver nitrate, silver carbonate, or silver chloride.

Also, the Step 3 can be performed by introducing a functionalized group as a result of: for example, reacting a carboxylic group in side chains of the polymer chains with an amine compound to form an amide bond; or reacting a carboxylic group in side chains of the polymer chains with a hydroxy group-containing compound to form an ester bond.

The functionalized group is preferably a fluoroalkyl group.

The amine compound is preferably a compound represented by the following formula:

$$CF_3(CF_2)_n-(CX_2)_p-NH_{2-m}((CF_2)_nCF_3)_m$$

wherein X represents hydrogen or fluorine; the n's are the same as or different from each other and each represent an integer of 1 to 10; m represents an integer of 0 to 2; and p represents an integer of 0 to 4.

Preferably, the (liquid) radical polymerizable monomers or a solution thereof contains a polymerization inhibitor, and the monomers are polymerized in the presence of the polymerization inhibitor. The polymerization inhibitor is preferably 4-methylphenol.

The polymer chains are preferably 10 to 50000 nm in length.

The present invention also relates to a surface-modified elastic body, which is obtained by the surface modification method.

The present invention also relates to a surface-modified elastic body, which needs to have sliding properties, low friction, or low water drag in the presence of water or in a dry state, and which is obtained by the surface modification method.

The present invention also relates to a surface-modified elastic body, which needs to have antibacterial properties and which is obtained by the surface modification method.

The present invention also relates to a surface-modified elastic body, which includes a three-dimensional solid and has at least partially a surface modified by the surface modification method.

The surface-modified elastic body is preferably a polymer brush.

The present invention also relates to a gasket for syringes, which has at least partially a surface modified by the surface modification method.

The present invention also relates to a catheter, which has at least partially a surface modified by the surface modification method.

The present invention also relates to a tire, which has at least partially a groove surface modified by the surface modification method.

Advantageous Effects of Invention

Since the surface modification method according to the present invention includes: Step 1 of forming polymerization initiation points on the surface of a rubber vulcanizate or a thermoplastic elastomer (object to be modified); Step 2 of radical polymerizing monomers starting from the polymerization initiation points to grow polymer chains on the surface of the object to be modified; and Step 3 of functionalizing the polymer chains, desired functions can be imparted to the polymer chains and therefore a surface-modified elastic body with various functions such as sliding properties and antibacterial properties can be provided easily.

DESCRIPTION OF EMBODIMENTS

The present invention relates to a surface modification method for modifying a rubber vulcanizate or a thermoplastic elastomer as an object to be modified, the method including: Step 1 of forming polymerization initiation points on the surface of the object to be modified; Step 2 of radical polymerizing monomers starting from the polymerization initiation points to grow polymer chains on the surface of the object to be modified; and Step 3 of functionalizing the polymer chains.

Monomers such as acrylic acid are polymerized on the surface of the object to be modified to form polymer chains, and these polymer chains can be used to impart a function such as sliding properties. On the other hand, the polymer chains of polyacrylic acid to be formed may disadvantageously have an acidic surface due to a carboxyl group in their side chains. In this case, when applied to, for example, gaskets for syringes, the polymer chains may affect liquid medicaments, and when applied to catheters, it may affect the body's internal environment such as proteins. Therefore, the surface of the polymer chains is preferably neutral or cationic, preferably while having another property such as hydrophobicity. In addition, since articles to be inserted into the body (e.g. catheters) require antibacterial properties, it is also preferable to introduce silver or the like onto the surface to impart such a function.

Since the surface modification method according to the present invention includes forming polymer chains on the surface of the object to be modified, and then subjecting the polymer chains to functionalization such as neutralization, hydrophobization, cationization, or antibacterial treatment, a polymer brush can be provided with desired performances and functions according to its use. Therefore, sliding properties, durability to repeated sliding motion, and sealing properties can be imparted, and antibacterial properties and hydrophobicity can also be imparted via treatment with silver, a fluorine compound or the like. In addition, other functionalization (e.g. neutralization, cationization) can also be achieved, for example, by a method including reacting a compound having such a function with the polymer chains. Thus, the present invention can easily provide surface-modified elastic bodies with desired functions, such as gaskets for syringes, catheters, and tires.

In the Step 1, polymerization initiation points are formed on the surface of vulcanization-molded rubber or molded thermoplastic elastomer (object to be modified).

Preferred examples of the rubber vulcanizate and the thermoplastic elastomer include those containing a carbon atom adjacent to a double bond (allylic carbon atom).

Examples of rubber for the object to be modified include diene rubbers such as styrene-butadiene rubber, butadiene rubber, isoprene rubber, natural rubber, and deproteinized natural rubber; and butyl rubber and halogenated butyl rubber which have a degree of unsaturation of a few percent of isoprene units. In the case of the butyl rubber or halogenated butyl rubber, rubber cross-linked by triazine is preferred because the amount of matter extracted from the rubber vulcanizate is small. In this case, the rubber may contain an acid acceptor, and examples of suitable acid acceptors include hydrotalcites and magnesium carbonate.

In the case of other rubbers, sulfur vulcanization is preferred. In such a case, compounding agents commonly used for sulfur vulcanization may be added, such as a vulcanization accelerator, zinc oxide, filler, and a silane coupling agent. Preferred examples of the filler include carbon black, silica, clay, talc, and calcium carbonate.

The vulcanization conditions for rubber may be appropriately adjusted. The vulcanization temperature for rubber is preferably 150° C. or higher, more preferably 170° C. or higher, and further preferably 175° C. or higher.

Examples of the thermoplastic elastomer include polymer compounds having rubber elasticity at room temperature owing to aggregates of plastic components (hard segments) that serve as crosslinking points (e.g. thermoplastic elastomers (TPE) such as styrene-butadiene-styrene copolymers); and polymer compounds having rubber elasticity, obtained by mixing thermoplastic components and rubber components and dynamically crosslinking the mixture by a crosslinking agent (e.g. thermoplastic elastomers (TPV) such as polymer alloys containing a styrenic block copolymer or olefinic resin together with crosslinked rubber components).

Other suitable examples of the thermoplastic elastomer include nylon, polyester, polyurethane, polypropylene, and dynamically-crosslinked thermoplastic elastomers thereof. In the case of dynamically-crosslinked thermoplastic elastomers, preferred are those obtained by dynamically crosslinking halogenated butyl rubber in a thermoplastic elastomer. Here, the thermoplastic elastomer is preferably nylon, polyurethane, polypropylene, or SIBS (styrene-isobutylene-styrene block copolymer), for example.

The polymerization initiation points may be formed by adsorption of a photosensitizer on the surface of the object to be modified, for example. Examples of the photosensitizer include carbonyl compounds, organic sulfur compounds (e.g. tetraethylthiuramdisulfide), persulfides, redox compounds, azo compounds, diazo compounds, halogen compounds, and photoreductive pigments. Preferred among these are carbonyl compounds.

The carbonyl compound as a photosensitizer is preferably benzophenone or its derivative, and suitable examples thereof include benzophenone compounds represented by the following formula (1):

wherein $R^1$ to $R^5$ and $R^{1'}$ to $R^{5'}$ are the same as or different from each other and each represent a hydrogen atom, an alkyl group, a halogen (fluorine, chlorine, bromine, iodine), a hydroxy group, a primary, secondary, or tertiary amino group, a mercapto group, or a hydrocarbon group that may contain an oxygen atom, a nitrogen atom, or a sulfur atom; and any two adjacent groups thereof may be joined to each other to form a cyclic structure together with the carbon atoms to which they are bonded.

Specific examples of the benzophenone compounds include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone because they contribute to favorable polymer brushes.

Fluorobenzophenone compounds may also be suitably used as the benzophenone compound. Examples thereof include 2,3,4,5,6-pentafluorobenzophenone and decafluorobenzophenone respectively represented by the following formulae.

The adsorption of a photosensitizer (e.g. benzophenone compounds) on the surface of the object to be modified may be achieved by a known method. For example, in the case of using a benzophenone compound, polymerization initiation points are formed as follows: the benzophenone compound is dissolved in an organic solvent to prepare a solution; a surface portion of the target object to be modified is treated with this solution so that the compound is adsorbed on the surface portion; and if necessary, the organic solvent is dried to be evaporated off. The surface-treating method is not particularly limited as long as the benzophenone compound solution can be brought into contact with the surface of the object to be modified. Suitable examples thereof include application of the benzophenone compound solution, spraying thereof, and immersion of the surface into the solution. If only a part of the surface needs to be modified, it is sufficient to adsorb the sensitizer only on such a part of the surface. In this case, for example, application of the solution or spraying of the solution is suitable. Examples of the solvent include methanol, ethanol, acetone, benzene, toluene, methyl ethyl ketone, ethyl acetate, and THF. Acetone is preferred because it does not swell the object to be modified and it is rapidly dried and evaporated off.

Alternatively, it is preferable to surface-treat the portion to be modified with the benzophenone compound solution so that the photosensitizer is adsorbed on the portion to be modified, and then irradiate it with light so that the photosensitizer is chemically bonded to the surface of the object to be modified. For example, ultraviolet rays at a wavelength of 300 to 450 nm (preferably 300 to 400 nm, more preferably 350 to 400 nm) may be irradiated to immobilize the benzophenone compound on the surface. In the Step 1 and this immobilization, hydrogen on the rubber surface is extracted and this extracted hydrogen bonds to the oxygen in a C=O bond of the benzophenone while the carbon in this C=O bond and carbon on the rubber surface form a covalent bond, so that a C—O—H bond is formed. This hydrogen-extracting reaction selectively occurs at allylic hydrogen in the object to be modified, and thus the rubber preferably contains butadiene or isoprene units which contain allylic hydrogen.

R: hydrogen or C1—C4 alkyl group

In particular, it is preferable to treat the surface of the object to be modified with the photosensitizer so that the photosensitizer is adsorbed on the surface, and then irradiate the treated surface with LED light at 300 to 400 nm to form a polymerization initiator. Especially, it is preferable to surface-treat the surface of the object to be modified with the benzophenone compound solution so that the photosensitizer is adsorbed on the surface, and then irradiate the treated surface with LED light at 300 to 400 nm so that the adsorbed photosensitizer is chemically bonded to the surface. The wavelength of LED light is suitably at 355 to 380 nm.

In the Step 2, monomers are radical polymerized starting from the polymerization initiation points to grow polymer chains on the surface of the object to be modified.

The monomers may be appropriately selected according to the properties and functions to be imparted to the polymer chains prepared in the Steps 2 and 3. Examples thereof include ionic monomers containing ionic groups at, for example, their substituents or side chains. In this case, the Step 2 provides polymer chains which exert a function such as sliding properties owing to the ionic monomers, and furthermore, the Step 3 can easily add other functions such as antibacterial properties and hydrophobicity.

Examples of the ionic monomers include monomers having a positive charge (cationic monomers), such as ammonium and phosphonium; and monomers containing an acidic group which has a negative charge or can be dissociated into a negative charge (e.g. a sulfonate group, a carboxyl group, a phosphate group, a phosphonate group) (anionic monomers).

Specific examples of the ionic monomers include acrylic acid, methacrylic acid, itaconic acid, 3-vinylpropionic acid, vinylsulfonic acid, 2-sulfoethyl(meth)acrylate, 3-sulfopropyl (meth)acrylate, 2-acrylamide-2-methylpropanesulfonic acid, and styrenesulfonic acid; allylamine, and 2-dimethylaminoethyl(meth)acrylate; 3-trimethylammoniumpropyl(meth) acrylate, and 3-trimethylammoniumpropyl(meth)acrylamide. Preferred among these are acrylic acid and methacrylic acid because they allow various functions to be imparted in the Steps 2 and 3. Each of these may be used alone, or two or more of these may be used in combination.

As an example of to the method of radical polymerizing monomers in the Step 2, to the surface of the object to be modified on which the benzophenone compound or the like is adsorbed or covalently bonded, (liquid) monomers or a solution thereof is applied (sprayed), or the object to be modified is immersed into (liquid) monomers or a solution thereof; and then light such as ultraviolet rays is irradiated so that radical polymerization (photoradical polymerization) proceeds, whereby polymer chains are grown on the surface of the object to be modified. Alternatively, after the application, the surface may be covered with a transparent glass, PET, polycarbonate, or the like; then, light such as ultraviolet rays is irradiated thereto so that radical polymerization (photoradical polymerization) proceeds, whereby polymer chains are grown on the surface of the object to be modified.

In the Step 2, it is preferable to allow radical polymerization (photoradical polymerization) to proceed by light irradiation to the monomers with a reducing agent or an antioxidant added thereto. This case is preferred because the reducing agent or antioxidant captures oxygen in the system. In the monomers with a reducing agent or an antioxidant added thereto, the components may be mixed with or may be separated from each other. Further, the object to be modified obtained in the Step 1 may be brought into contact with the monomers before the reducing agent or antioxidant is added thereto, or alternatively the components may be mixed in advance before the mixed material is brought into contact with the object to be modified.

Specifically, radical polymerization is performed to form polymer chains by light irradiation after the following processes: that is, the object to be modified obtained in the Step 1, on a surface of which the polymerization initiation points are formed from the photosensitizer, is brought into contact (e.g. immersion, application) with (liquid) monomers or a solution thereof with a solution of a reducing agent or an antioxidant added thereto; or alternatively, the object to be modified is brought into contact with (liquid) monomers or a solution thereof, and then a solution of a reducing agent or an antioxidant is put thereon.

The reducing agent and the antioxidant are not particularly limited, and compounds having such effect can be appropriately used. Examples thereof include vitamin A series such as retinol, dehydroretinol, retinol acetate, retinol palmitate, retinal, retinoic acid, and vitamin A oil, and derivatives and salts thereof; carotenoids such as α-carotene, β-carotene, γ-carotene, cryptoxanthin, astaxanthin, and fucoxanthin, and derivatives thereof; vitamin B series such as pyridoxine, pyridoxal, pyridoxal-5-phosphate, and pyridoxamine, and derivatives and salts thereof; vitamin C series such as ascorbic acid, sodium ascorbate, ascorbyl stearate, ascorbyl palmitate, ascorbyl dipalmitate, and magnesium ascorbyl phosphate, and derivatives and salts thereof; vitamin D series such as ergocalciferol, cholecalciferol, and 1,2,5-dihydroxy-cholecalciferol, and derivatives and salts thereof; vitamin E series such as α-tocopherol, β-tocopherol, γ-tocopherol, δ-tocopherol, α-tocotrienol, β-tocotrienol, γ-tocotrienol, δ-tocotrienol, tocopherol acetate, and tocopherol nicotinate, and derivatives and salts thereof; trolox, and derivatives and salts thereof; dihydroxytoluene, butylhydroxytoluene, butylhydroxyanisole, dibutylhydroxytoluene, α-lipoic acid, dehydrolipoic acid, and glutathione, and derivatives and salts thereof; uric acid, and erythorbic acid and their derivatives and salts, such as erythorbic acid and sodium erythorbate; gallic acid, and derivatives and salts thereof, such as gallic acid and propyl gallate; rutin, and derivatives and salts thereof, such as rutin and α-glycosyl-rutin; tryptophan, and derivatives and salts thereof; histidine, and derivatives and salts thereof; cysteine derivatives and salts thereof such as N-acetylcysteine, N-acetylhomocysteine, N-octanoylcysteine, and N-acetylcysteine methyl ester; cystine derivatives and salts thereof such as N,N'-diacetylcystine dimethyl ester, N,N'-dioctanoylcystine dimethyl ester, and N,N'-dioctanoylhomocystine dimethyl ester; carnosine, and derivatives and salts thereof; homocarnosine, and derivatives and salts thereof; anserine, and derivatives and salts thereof; carcinine, and derivatives and salts thereof; dipeptide or tripeptide derivatives containing histidine and/or tryptophan and/or histamine, and salts thereof; flavonoids such as flavanone, flavone, anthocyanin, anthocyanidin, flavonol, quercetin, quercitrin, myricetin, fisetin, hamamelitannin, catechin, epicatechin, gallocatechin, epigallocatechin, epicatechin gallate, and epigallocatechin gallate; tannic acid, caffeic acid, ferulic acid, protocatechuic acid, calcone, oryzanol, carnosol, sesamol, sesamine, sesamolin, zingerone, curcumin, tetrahydrocurcumin, clovamide, deoxyclovamide, shogaol, capsaicine, vanillylamide, ellagic acid, bromphenol, flavoglaucin, melanoidin, riboflavin, riboflavin butyrate, flavin mononucleotide, flavin adenine nucleotide, ubiquinone, ubiquinol, mannitol, bilirubin, cholesterol, ebselen, selenomethionine, ceruloplasmin, transferrin, lactoferrin, albumin, superoxide dismutase, catalase, glutathione peroxidase, metallothionein, and O-phosphono-pyridoxylidene rhodamine. Each of these may be used alone, or two or more of these may be used in combination.

Preferred among these are riboflavin, ascorbic acid, α-tocopherol, β-carotene, and uric acid, and particularly preferred are riboflavin and ascorbic acid, because they capture oxygen well.

In the case of using a solution of a reducing agent or an antioxidant, the concentration of the reducing agent or antioxidant is preferably $10^{-4}$ to 1% by mass, and more preferably $10^{-3}$ to 0.1% by mass.

The amount of the radical polymerizable monomers may be appropriately adjusted depending on, for example, a desired length of polymer chains to be formed and desired performance to be achieved by the chains. Also, the amount of the reducing agent or antioxidant may be appropriately adjusted from the viewpoint of the ability to capture oxygen in the system, for example.

With respect to the solvent to be applied (sprayed), the method for applying (spraying) the solvent, the method of immersion, the conditions for irradiation, and the like, conventionally known materials and methods may be used. The solution of radical polymerizable monomers is an aqueous solution or a solution prepared by dissolving the monomers in an organic solvent that does not dissolve a photosensitizer (e.g. benzophenone compounds) to be used. Further, as the (liquid) radical polymerizable monomers or a solution thereof, those containing known polymerization inhibitors (e.g. 4-methylphenol) may be used.

In the present invention, radical polymerization of monomers is allowed to proceed by light irradiation after the (liquid) monomers or a solution thereof is applied to the object to be modified, or the object to be modified is immersed in the monomers or a solution thereof. Here, UV light sources may be suitably used, such as high-pressure mercury lamps, metal halide lamps, and LED lamps, each of which has an emission wavelength mainly in the range of ultraviolet rays. The light dose may be appropriately adjusted in consideration of the polymerization time and uniform progress of the reaction. In order to prevent polymerization inhibition due to active gas such as oxygen in a reaction container, it is preferable to remove oxygen in the reaction container and the reaction solution during or before light irradiation. Thus, for example, a method may appropriately be employed in which inert gas such as nitrogen gas or argon gas is inserted into the reaction container and the reaction solution to discharge active gas such as oxygen from the reaction system to replace the atmosphere in the reaction system with the inert gas. In addition, in order to prevent reaction inhibition due to oxygen or the like, for example, measures may appropriately be used in which a UV light source is placed such that no air layer (oxygen content: 15% or higher) exists between the reaction container made of glass, plastics or the like and the reaction solution or the object to be modified.

In the case of irradiation with ultraviolet rays, the wavelength is preferably at 300 to 450 nm, and more preferably at 300 to 400 nm. This enables polymer chains to be favorably formed on the surface of the object to be modified. The light source may be a high-pressure mercury lamp, an LED with a center wavelength of 365 nm, an LED with a center wavelength of 375 nm, or the like. In particular, preferred is irradiation with LED light at 300 to 400 nm, and more preferred is irradiation with LED light at 355 to 380 nm. Especially, from the viewpoint of efficiency, preferred are LEDs with a center wavelength of 365 nm which is close to the excitation wavelength of benzophenone (366 nm), for example.

The length of the polymer chains formed in the Step 2 is preferably 10 to 50000 nm, and more preferably 100 to 50000 nm. Chains shorter than 10 nm are unlikely to provide good sliding properties. Chains longer than 50000 nm are unlikely to be expected to provide better sliding properties and thus are likely to increase the cost of raw materials because expensive monomers are used. In addition, a surface pattern formed by the surface treatment is likely to be visible to naked eye, which tends to spoil the beauty and to decrease the sealing properties.

In the Step 2, two or more species of monomers may be radical polymerized starting from the polymerization initiation points, and multiple kinds of polymer chains may be grown on the surface of the object to be modified. The surface modification method of the present invention may include cross-linking between polymer chains. In this case, ionic cross-linking, cross-linking by a hydrophilic group containing an oxygen atom, or cross-linking by a compound containing a halogen group (e.g. iodine), may be carried out between the polymer chains.

In the Step 3, the polymer chains formed in the Step 2 are functionalized. This Step 3 is to add another function to the formed polymer chains. That is, desired performance and function are added by an appropriately selected method, for example, by salification of a functional group in side chains of the polymer chains after, if necessary, the functional group is brought into contact with aqueous ammonia or the like, or alternatively by reaction of the functional group with a compound containing a functionalized group such as another functional group. Therefore, a surface-modified elastic body simultaneously having various functions can be prepared.

For example, in order to impart antibacterial properties to polymer chains of poly(meth)acrylic acid that are prepared by polymerizing acrylic acid and/or methacrylic acid in the Step 2, in the Step 3, the poly(meth)acrylic acid may be salified with an antibacterial metal salt to add an antibacterial metal to the polymer chains. The salification may be performed by a known method; for example, it may be performed by a method (e.g. immersion, application) of bringing the polymer chains into contact with an aqueous solution of an antibacterial metal salt (e.g. an aqueous solution of a silver salt, aqueous ammonia, a solution of gold in aqua regia).

Examples of the antibacterial metal salt include sulfates, carbonates, acetates, nitrates, halogenated salts, and hydroxides of antibacterial metals such as gold, silver, copper, platinum, zinc, nickel, manganese, cobalt, and tin. In particular, silver salts are suitable because they are easily available at low cost and highly safe.

Specific examples of the silver salts (silver compounds) include organic acid silver salts such as silver acetate, silver carbonate, silver formate, silver propionate, silver butyrate, silver citrate, and silver lactate; silver halides such as silver chloride, silver iodide, silver bromide, and silver fluoride; and inorganic acid silver salts such as silver carbonate, silver sulfate, silver nitrate, silver nitrite, silver chlorate, and silver perchlorate. Specific examples of the zinc salts (zinc compounds) include zinc sulfate, zinc chloride, and zinc acetate. Specific examples of the copper salts (copper compounds) include copper sulfate, copper chloride, copper hydroxide, and copper acetate. In addition, other known metal salts such as those of gold, platinum, nickel, manganese, cobalt, and tin may be used. Each of these may be used alone, or two or more of these may be used in combination.

In order to impart alkalinity, neutrality, or cationicity to polymer chains of poly(meth)acrylic acid that are prepared in the Step 2, in the Step 3, the poly(meth)acrylic acid may be salified with an alkaline salt to add an alkaline metal to the polymer chains. The salification may be performed by a known method; for example, it may be performed by a method of bringing the polymer chains into contact with an aqueous solution of an alkaline salt.

Examples of the alkaline salt include alkali metal salts such as sodium, potassium, and lithium salts; and alkaline earth metal salts such as magnesium and calcium salts. Specific examples of the alkali metal salts include inorganic acid salts, carbonates, and phosphates of alkali metals, such as lithium chloride, lithium nitrate, lithium sulfate, lithium carbonate, lithium perchlorate, sodium chloride, sodium hydrogen carbonate, sodium nitrate, sodium carbonate, sodium sulfate, sodium sulfite, sodium perchlorate, potassium nitrate, potassium sulfate, potassium carbonate, potassium chloride, and potassium bromide. Specific examples of the alkaline earth metal salts include inorganic acid salts, carbonates, and phosphates of alkaline earth metals, such as calcium sulfate, calcium nitrate, calcium chloride, and magnesium sulfate. Each of these may be used alone, or two or more of these may be used in combination.

Also, after polymer chains of poly(meth)acrylic acid are prepared in the Step 2, the poly(meth)acrylic acid and an amine compound may be subjected to an amidation reaction to introduce a functionalized group (e.g. various functional groups) present in the amine compound in the Step 3. For example, in order to impart hydrophobicity to the polymer chains prepared in the Step 2, in the Step 3, the poly(meth)acrylic acid and a fluorinated amine compound may be subjected to an amidation reaction to add the fluorinated amine compound to the polymer chains. The amidation may be performed by a known method; for example, it may be performed by a method in which a carboxyl group of the polymer chains is reacted with the amino group of an amine compound (e.g. fluorinated amine compounds) in the presence of an acid such as sulfuric acid so that a functionalized group (functional group) such as a fluoroalkyl group is introduced. Alternatively, for example, the amidation may be performed by a method of condensing a carboxyl group of the polymer chains and the amino group of an amine compound (e.g. fluorinated amine compounds) using a condensing agent, or a method of chlorinating a carboxyl group of the polymer chains with thionyl chloride and then condensing the chlorinated carboxyl group and the amino group of the amine compound under basic conditions, such as in the presence of sodium hydroxide.

Further, after polymer chains of poly(meth)acrylic acid are prepared in the Step 2, the poly(meth)acrylic acid and a hydroxy group-containing compound may be subjected to an esterification reaction to introduce a functionalized group (e.g. various functional groups) present in the hydroxy group-containing compound in the Step 3. For example, the esterification may be performed by a method of condensing a carboxyl group of the polymer chains and the hydroxy group of a hydroxy group-containing compound (e.g. fluorinated hydroxy-group-containing compounds) in the presence of an acid.

The fluorinated amine compound may be a fluorinated organic aliphatic amine, for example, and examples thereof include compounds represented by the following formula:

wherein X represents hydrogen or fluorine; the n's are the same as or different from each other and each represent an integer of 1 to 10; m represents an integer of 0 to 2; and p represents an integer of 0 to 4.

Specific examples of the fluorinated aliphatic amine include 2,2,2-trifluoroethylamine, 2,2,3,3,3-pentafluoropropylamine, 2,2,3,3,4,4,4-heptafluorobutylamine, 2,2,3,3,4,4,5,5,5-nonafluoropentylamine, 2,2,3,3,4,4,5,5,6,6,6-undecafluorohexylamine, trifluoromethylamine, perfluoroethylamine, perfluoropropylamine, perfluorobutylamine, perfluoropentylamine, perfluorohexylamine, perfluoroheptylamine, perfluorooctylamine, perfluorodecylamine, and difluoroethanolamine. Each of these may be used alone or two or more of these may be used in combination.

Examples of the fluorinated hydroxyl-group-containing compounds include 1H,1H-heptafluorobutan-1-ol ($CF_3CF_2CF_2CH_2OH$), 1H,1H-nonafluoropentan-1-ol ($CF_3(CF_2)_3CH_2OH$), 1H, 1H-perfluorononan-1-ol ($CF_3(CF_2)_7CH_2OH$), 1H,1H-2,5-bis(trifluoromethyl)-3,6-dioxaper fluorononanol ($CF_3CF_2CF_2OCF(CF_3)CF_2OCF(CF_3)CH_2OH$), 3,3,3-trifluoropropan-1-ol ($CF_3CH_2CH_2OH$), 3,3,4,4,4-pentafluorobutan-1-ol ($CF_3CF_2CH_2CH_2OH$), 3,3,4,4-tetrafluoro-3-(trifluoromethyl)butan-1-ol ($CF_3CF(CF_3)CH_2CH_2OH$), 1H,1H,2H,2H-nonafluorohexan-1-ol ($CF_3(CE_2)_3CH_2CH_2OH$), 1H,1H,2H,3H,3H-perfluorononane-1,2-diol ($CF_3(CF_2)_5CH_2CH(OH)CH_2OH$), and 1H,1H,2H,3H,3H-perfluoroundecane-1,2-diol ($CF_3(CF_2)_7CH_2CH(OH)CH_2OH$). Each of these may be used alone, or two or more of these may be used in combination.

Application of the surface modification method to a rubber vulcanizate or a thermoplastic elastomer enables to provide a surface-modified elastic body. For example, a surface-modified elastic body excellent in sliding properties in the presence of water or in a dry state can be obtained, and it is also excellent in that it shows low friction and low water resistance or drag. In addition, the elastic body can be imparted a desired function such as an antibacterial metal salt, hydrophobicity, neutrality, or cationicity. Also, application of the above method to at least part of a three-dimensional solid (e.g. elastic body) enables to provide a surface-modified elastic body. Preferred examples of the surface-modified elastic body include polymer brushes. The polymer brush mentioned here means a graft polymer obtained by the "grafting from" method by surface-initiated living radical polymerization. The graft chains are preferably oriented in a direction substantially vertical to the surface of the object to be modified because, in such a case, the entropy is reduced and the molecular mobility of the graft chains is reduced, which ensures sliding properties. Preferred are semidilute brushes and concentrated brushes which have a brush density of 0.01 chains/nm$^2$ or higher.

Furthermore, application of the surface modification method to a rubber vulcanizate or a thermoplastic elastomer enables to produce a gasket for syringes which has at least partially a modified surface. The modification is preferably performed at least on the sliding portion of the gasket surface, and it may be performed on the entire surface.

Figure 1:
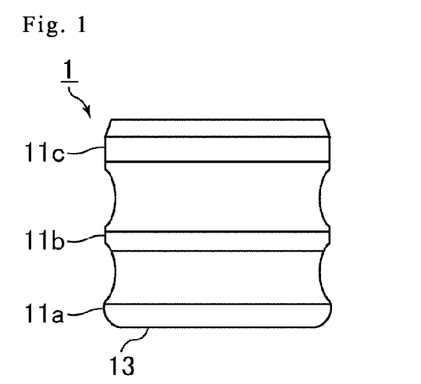
FIG. 1 is a side view of one embodiment of gaskets for syringes.

FIG. 1 is a side view of one embodiment of gaskets for syringes. A gasket 1 shown in FIG. 1 has three circular protruding portions 11a, 11b, and 11c, continuously protruding in the circumferential direction, on the outer periphery that is to contact with the inner periphery of a syringe barrel. Examples of the portion of the gasket 1 to which the surface modification is applied include (1) the surface of protruding portions that is to contact with a syringe barrel, such as the circular protruding portions 11a, 11b, and 11c; (2) the entire side surface including the circular protruding portions 11a, 11b, and 11c; and (3) the entire side surface and a bottom surface 13.

Similarly, application of the surface modification method to a rubber vulcanizate or a thermoplastic elastomer enables to produce a catheter having at least partially a modified surface. The modification is preferably performed at least on a portion that is to contact with body fluid, such as the outer surface of the catheter, and it may be performed on the entire surface.

Further, application of the surface modification method to grooves formed on the tread of a tire for use on vehicles such as passenger cars to form a polymer brush on the grooves enables to reduce the fluid resistance of the groove surface on wet or snowy roads and to increase the contact angle with water. Therefore, the abilities to remove and drain water or snow are enhanced and the grip performance is improved.

Figure 2:
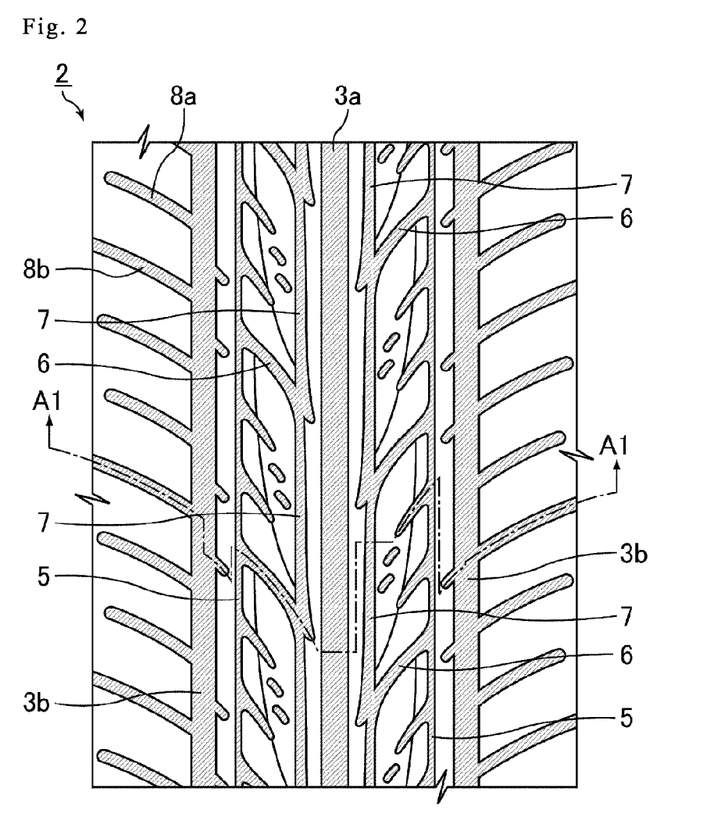
FIG. 2 is a development view of one example of the tread portion of pneumatic tires (the whole tire is not illustrated).
Figure 3:
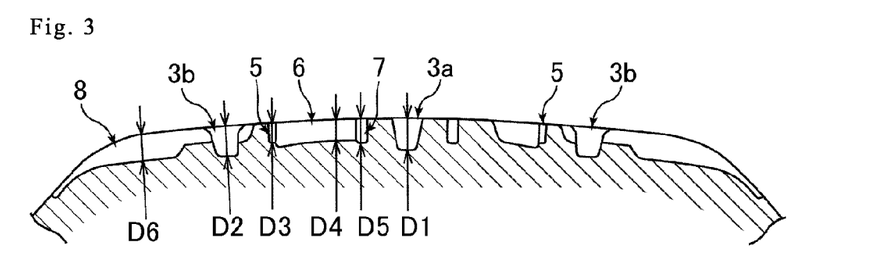
FIG. 3 is an A1-A1 cross-sectional view of one example of FIG. 2.

FIG. 2 is a development view of one example of the tread portion 2 of pneumatic tires (the whole tire is not illustrated), and FIG. 3 is an A1-A1 cross-sectional view of one example of FIG. 2.

In FIGS. 2 and 3, a longitudinal center groove 3a (groove depth D1) and longitudinal shoulder grooves 3b (groove depth D2) are straight grooves straightforwardly extending in the tire circumferential direction. Such straight grooves may contribute to low resistance to drainage and high drainage performance upon straight running.

The pneumatic tire also has fine grooves 5 (groove depth D3) extending in the tire circumferential direction on the side of the longitudinal shoulder groove 3b; beveled intermediate grooves 6 (groove depth D4) extending with an upward slope from the fine groove 5 toward the longitudinal center groove 3a, which are located at a position inner than the fine groove 5 in the tire axis direction, and also located next to each other in the tire circumferential direction; connecting grooves 7 (groove depth D5) connecting the grooves 6; and lateral shoulder grooves 8, 8a, and 8b (groove depth D6) extending from the longitudinal shoulder groove 3b toward the outside; and the like, and these grooves may also contribute to drainage performance. Application of the above method to these grooves enables to produce the aforementioned effects.

EXAMPLES

The following will describe the present invention in greater detail based on, but not limited to, examples.

Example 1

A chlorobutyl rubber (degree of unsaturation: 1 to 2%) having isoprene units was cross-linked by triazine to give a rubber vulcanizate (vulcanized at 180° C. for 10 minutes). The rubber vulcanizate was immersed in a 1 wt % acetone solution of benzophenone so that the benzophenone was adsorbed onto the surface of the rubber vulcanizate. Then, the rubber vulcanizate was taken out and dried. The surface of the rubber vulcanizate was then irradiated with LED light at a wavelength of 365 nm for 10 minutes so that the benzophenone was chemically bonded to the surface. Next, the surface was washed with acetone to remove unreacted benzophenone.

The dried rubber vulcanizate was immersed in an acrylic acid aqueous solution (2.5 M: 18 g of acrylic acid was dissolved in 100 mL of water) in a glass reaction container, and a riboflavin aqueous solution (concentration: 0.0093 mmol/L) was poured thereonto. Since the latter aqueous solution was not miscible with the monomer solution and also had a lower specific gravity than the monomer solution, the latter aqueous solution was separated as an upper layer. Then, ultraviolet rays were irradiated for 1 hour using an LED light at a wavelength of 365 nm to cause radical polymerization, so that polymer chains were grown on the rubber surface.

The obtained rubber vulcanizate with polymer chains formed on the surface thereof was immersed in a silver nitrate aqueous solution (0.01 M) for 5 hours. Thereafter, the rubber vulcanizate was washed with water and dried to prepare a surface-modified elastic body (polymer brush).

Example 2

A surface-modified elastic body (polymer brush) was prepared in the same manner as in Example 1, except that the obtained rubber vulcanizate with polymer chains formed on the surface thereof was immersed in aqueous ammonia for 2 hours, washed with water, and then immersed in a silver nitrate aqueous solution.

Example 3

A surface-modified elastic body (polymer brush) was prepared in the same manner as in Example 1, except that an ammonia/dilute nitric acid aqueous solution of silver carbonate was used instead of the silver nitrate aqueous solution.

Example 4

A surface-modified elastic body (polymer brush) was prepared in the same manner as in Example 1, except that an ammonia aqueous solution of silver chloride was used instead of the silver nitrate aqueous solution.

Example 5

A chlorobutyl rubber (degree of unsaturation: 1 to 2%) having isoprene units was cross-linked by triazine to give a rubber vulcanizate (vulcanized at 180° C. for 10 minutes).

The rubber vulcanizate was immersed in a 1 wt % acetone solution of benzophenone so that the benzophenone was adsorbed on the surface of the rubber vulcanizate. Then, the rubber vulcanizate was taken out and dried. The surface of the rubber vulcanizate was irradiated with LED light at a wavelength of 365 nm for 10 minutes so that the benzophenone was chemically bonded to the surface. Next, the surface was washed with acetone to remove unreacted benzophenone.

The dried rubber vulcanizate was immersed in an acrylic acid aqueous solution (2.5 M: 18 g of acrylic acid was dissolved in 100 mL of water) in a glass reaction container, and a riboflavin aqueous solution (concentration: 0.0093 mmol/L) was poured thereonto. Since the latter aqueous solution was not miscible with the monomer solution and also had a lower specific gravity than the monomer solution, it was separated as an upper layer. Then, ultraviolet rays were irradiated for 1 hour using an LED light at a wavelength of 365 nm to cause radical polymerization, so that polymer chains were grown on the rubber surface.

With respect to the obtained rubber vulcanizate with polymer chains formed on the surface thereof, the side-chain carboxyl group (COOH group) of the acrylic acid polymerized on the surface was amidated with 1H,1H-perfluoroheptylamine ($CF_3(CF_2)_5CH_2NH_2$) in the presence of sulfuric acid (for 6 hours), and then the amidated product was washed. Thus, a surface-modified elastic body (polymer brush) was prepared.

Comparative Example 1

A rubber vulcanizate (vulcanized at 180° C. for 10 minutes) prepared by cross-linking a chlorobutyl rubber by triazine was used.

The surface-modified elastic bodies prepared in the examples and the comparative example were evaluated by the following methods.

Length of Polymer Chains

The length of polymer chains formed on the surface of the rubber vulcanizate was measured on a cross section of the modified rubber vulcanizate with polymer chains formed thereon by using a SEM at an accelerating voltage of 15 kV and a magnification of 1000 times. The thickness of the polymer layer photographed was treated as the length of the polymer chains.

Coefficient of Static Friction and Coefficient of Dynamic Friction

The coefficients of static friction and dynamic friction of the surface of the surface-modified elastic body and the coefficients of static friction and dynamic friction of the surface of the sample with 200 μL of water dripped thereon were measured in conformity with the method described in ASTM D1894. Further, the sample was brought into contact with borosilicate glass and the friction with borosilicate glass was measured. The measurement of the coefficients of friction was performed under the following conditions: load 200 g, tensile rate 600 mm/min, and load distance 10 cm. The device used here was HEIDON type 14 (Shinto Scientific Co., Ltd.).

Analysis of Silver

With respect to the polymer brushes prepared in the examples, introduction of silver was confirmed by elemental analysis using SEM-EDX.

TABLE 1

|  | Examples | | | | | Comparative Example |
|---|---|---|---|---|---|---|
|  | 1 | 2 | 3 | 4 | 5 | 1 |
| Length of polymer chains (nm) | 4500 | 4400 | 4500 | 4600 | 4600 | — |
| Coefficient of static friction | 0.76 | 0.78 | 0.80 | 0.77 | 0.81 | 2.03 |
| Coefficient of dynamic friction | 0.51 | 0.49 | 0.52 | 0.48 | 0.50 | 1.45 |
| Coefficient of static friction 30 seconds after dripping water | 0.33 | 0.32 | 0.33 | 0.30 | 0.31 | 1.78 |
| Coefficient of dynamic friction 30 seconds after dripping water | 0.15 | 0.16 | 0.16 | 0.13 | 0.16 | 1.24 |
| Introduction of silver | Comfirmed | Comfirmed | Comfirmed | Comfirmed | Comfirmed | — |

In each example, the surface of the surface-modified elastic body had greatly reduced coefficients of static friction and dynamic friction, and good sliding properties were showed. Also, since only the surface was modified, the sealing properties were equal to that in Comparative Example 1. In addition, it was confirmed that silver was introduced into the elastic bodies in the examples.

Thus, in the case that the present invention is applied to gaskets for syringe plungers, sufficient sealing properties are achieved while the friction of the plunger with the syringe barrel is reduced, whereby treatment using such a syringe can be easily and accurately performed. Further, since the difference between the coefficient of static friction and the coefficient of dynamic friction is small, start of pushing the plunger and the subsequent approaching of the plunger are smoothly performed without pulsation. Similarly, in the case that a syringe barrel is formed from a thermoplastic elastomer and polymer chains are formed on its inner surface, treatment using the syringe is easily performed.

In the case that the present invention is applied to catheters, not only sliding properties but also antibacterial properties owing to silver are ensured. In addition, since salification is performed, less bad influence is caused in liquid medicaments and in the body.

Furthermore, the aforementioned effects can be expected when polymer chains are formed on the surface of grooves formed on treads, and sidewalls of tires used on vehicles such as passenger cars, or on the surface of diaphragms, sliding surfaces of skis and snowboards, swimsuits, road signs, sign boards, and the like.

REFERENCE SIGNS LIST

1: gasket
11a, 11b, 11c: circular protruding portion
13: bottom surface
2: tread portion
3a: longitudinal center groove
3b: longitudinal shoulder groove
5: fine groove
6: beveled intermediate groove
7: connecting groove
8, 8a, 8b: lateral shoulder groove

The invention claimed is:
1. A surface modification method for modifying a rubber vulcanizate or a thermoplastic elastomer as an object to be modified, the method comprising:
Step 1 of forming polymerization initiation points on a surface of the object to be modified;
Step 2 of radical polymerizing monomers starting from the polymerization initiation points to grow polymer chains on the surface of the object to be modified; and
Step 3 of functionalizing the polymer chains,
wherein the rubber vulcanizate or the thermoplastic elastomer contains an allylic carbon atom which is a carbon atom adjacent to a double bond.
2. The surface modification method according to claim 1, wherein the Step 1 comprises irradiating the surface of the object to be modified with LED light at 300 to 400 nm to form the polymerization initiation points from a photosensitizer on the surface, and
the Step 2 comprises irradiating the monomers with LED light at 300 to 400 nm to radical polymerize the monomers starting from the polymerization initiation points to grow the polymer chains.
3. The surface modification method according to claim 2, wherein the photosensitizer is a benzophenone compound represented by the following formula (1):

(1)

wherein $R^1$ to $R^5$ and $R^{1\prime}$ to $R^{5\prime}$ are the same as or different from each other and each represent a hydrogen atom, an alkyl group, a halogen, a hydroxy group, a primary, secondary, or tertiary amino group, a mercapto group, or a hydrocarbon group that may contain an oxygen atom, a nitrogen atom, or a sulfur atom; and any two adjacent groups thereof may be joined to each other to form a cyclic structure together with the carbon atoms to which they are bonded.
4. The surface modification method according to claim 1, wherein the Step 2 comprises adding a reducing agent or an antioxidant for radical polymerization of the monomers.

5. The surface modification method according to claim 4, wherein the reducing agent or the antioxidant is at least one selected from the group consisting of riboflavin, ascorbic acid, α-tocopherol, β-carotene, and uric acid.
6. The surface modification method according to claim 2, wherein during or before the light irradiation, an inert gas is inserted into a reaction container and a reaction solution to replace the atmosphere therein with the inert gas, followed by polymerization.
7. The surface modification method according to claim 1, wherein the Step 3 comprises salifying side chains of the polymer chains.
8. The surface modification method according to claim 1, the Step 3 comprises salifying side chains of the polymer chains using an alkali metal salt or an antibacterial metal salt.
9. The surface modification method according to claim 1, wherein the Step 3 comprises bringing side chains of the polymer chains into contact with aqueous ammonia and then salifying the side chains.
10. The surface modification method according to claim 1, wherein the Step 3 comprises salifying side chains of the polymer chains using an alkaline salt.
11. The surface modification method according to claim 1, wherein the Step 3 comprises salifying side chains of the polymer chains using a nitrate, a carbonate, or a halogenated salt.
12. The surface modification method according to claim 1, wherein the Step 3 comprises salifying side chains of the polymer chains using silver nitrate, silver carbonate, or silver chloride.
13. The surface modification method according to claim 1, wherein the Step 3 comprises reacting a carboxylic group in side chains of the polymer chains with an amine compound to form an amide bond so that a functionalized group is introduced.
14. The surface modification method according to claim 1, wherein the Step 3 comprises reacting a carboxylic group in side chains of the polymer chains with a hydroxy group-containing compound to form an ester bond so that a functionalized group is introduced.
15. The surface modification method according to claim 13, wherein the functionalized group is a fluoroalkyl group.
16. The surface modification method according to claim 13, wherein the amine compound is a compound represented by the following formula:

$CF_3(CF_2)_n-(CX_2)_p-NH_{2-m}((CF_2)_nCF_3)_m$ wherein X represents hydrogen or fluorine; the n's are the same as or different from each other and each represent an integer of 1 to 10; m represents an integer of 0 to 2; and p represents an integer of 0 to 4.
17. The surface modification method according to claim 1, wherein the (liquid) radical polymerizable monomers or a solution thereof contains a polymerization inhibitor, and the monomers are polymerized in the presence of the polymerization inhibitor.
18. The surface modification method according to claim 17, wherein the polymerization inhibitor is 4-methylphenol.
19. The surface modification method according to claim 1, wherein the polymer chains are 10 to 50000 nm in length.
20. A surface-modified elastic body, which is obtained by the surface modification method according to claim 1.

21. A surface-modified elastic body, which needs to have sliding properties, low friction, or low water drag in the presence of water or in a dry state, and which is obtained by the surface modification method according to claim 1.

22. A surface-modified elastic body, which needs to have antibacterial properties and which is obtained by the surface modification method according to claim 1.

23. A surface-modified elastic body, which comprises a three-dimensional solid and has at least partially a surface modified by the surface modification method according to claim 1.

24. The surface-modified elastic body according to claim 20, which is a polymer brush.

25. A gasket for syringes, which has at least partially a surface modified by the surface modification method according to claim 1.

26. A catheter, which has at least partially a surface modified by the surface modification method according to claim 1.

27. A tire, which has at least partially a groove surface modified by the surface modification method according to claim 1.

* * * * *